(12) United States Patent
Meggs

(10) Patent No.: US 11,449,847 B2
(45) Date of Patent: Sep. 20, 2022

(54) COMPUTING SYSTEM FOR SHARING NETWORKS PROVIDING VIRTUAL BILL ACCOUNT FEATURES AND RELATED METHODS

(71) Applicant: SHARABLE, LLC, Melbourne, FL (US)

(72) Inventor: Anthony F. Meggs, Melbourne, FL (US)

(73) Assignee: SHARABLE, LLC, Melbourne, FL (US)

( * ) Notice: Subject to any disclaimer, the term of this patent is extended or adjusted under 35 U.S.C. 154(b) by 98 days.

(21) Appl. No.: 15/931,767

(22) Filed: May 14, 2020

(65) Prior Publication Data

US 2020/0372554 A1 Nov. 26, 2020

Related U.S. Application Data

(60) Provisional application No. 62/869,661, filed on Jul. 2, 2019, provisional application No. 62/851,282, filed
(Continued)

(51) Int. Cl.
*G06Q 20/14* (2012.01)
*G06Q 40/02* (2012.01)
(Continued)

(52) U.S. Cl.
CPC ........... *G06Q 20/14* (2013.01); *G06Q 20/102* (2013.01); *G06Q 20/227* (2013.01);
(Continued)

(58) Field of Classification Search
None
See application file for complete search history.

(56) References Cited

U.S. PATENT DOCUMENTS 8,239,222 B2  8/2012 Meggs
8,583,548 B1 * 11/2013 Goldstein ............... G06Q 30/04
                                                      705/39
(Continued)

FOREIGN PATENT DOCUMENTS

WO   WO-2021146752 A1 *  7/2021  ............. G06Q 30/02

OTHER PUBLICATIONS

Huckstep, "Introducing the Third Wave of Peer-to-Peer Insurance", The Digital Insurer, Nov. 2018. (Year: 2018).*

*Primary Examiner* — Abdulmajeed Aziz
(74) *Attorney, Agent, or Firm* — Allen, Dyer, Doppelt + Gilchrist, PA

(57) ABSTRACT

A computing device may include a memory and a processor configured to cooperate therewith to operate a virtual share exchange (VSE) platform by establishing member sharing accounts on the VSE platform for respective members of the VSE platform for sharing payment of member healthcare bills across a plurality of the member sharing accounts, establishing healthcare provider accounts on the VSE platform for healthcare providers issuing the member healthcare bills, and receiving member healthcare bills issued by the healthcare providers and establishing a virtual bill account on the VSE platform for each member healthcare bill submitted for payment sharing. The virtual bill account may be externally addressable through a routing number and a unique account number associated therewith. The processor may further electronically transfer funds between the sharing accounts and to the healthcare provider that issued the member healthcare bill using the externally addressable routing number and unique account number.

10 Claims, 10 Drawing Sheets

Related U.S. Application Data on May 22, 2019, provisional application No. 62/851,395, filed on May 22, 2019, provisional application No. 62/851,321, filed on May 22, 2019, provisional application No. 62/851,279, filed on May 22, 2019, provisional application No. 62/851,298, filed on May 22, 2019.

(51) Int. Cl.

| | | |
|---|---|---|
| *G06Q 20/10* | (2012.01) | |
| *G06Q 20/22* | (2012.01) | |
| *G16H 50/70* | (2018.01) | |
| *G16H 70/20* | (2018.01) | |
| *G06Q 30/02* | (2012.01) | |
| *G06Q 40/08* | (2012.01) | |
| *G06Q 50/00* | (2012.01) | |
| *G06Q 30/04* | (2012.01) | |
| *G06Q 40/04* | (2012.01) | |
| *G16H 40/00* | (2018.01) | |
| *G06F 3/048* | (2013.01) | |

(52) U.S. Cl.
CPC ......... *G06Q 30/0205* (2013.01); *G06Q 30/04* (2013.01); *G06Q 40/02* (2013.01); *G06Q 40/025* (2013.01); *G06Q 40/04* (2013.01); *G06Q 40/08* (2013.01); *G06Q 50/01* (2013.01); *G16H 50/70* (2018.01); *G16H 70/20* (2018.01); *G06F 3/048* (2013.01); *G16H 40/00* (2018.01)

(56) References Cited

U.S. PATENT DOCUMENTS

| | | | |
|---|---|---|---|
| 2003/0078884 A1* | 4/2003 | Bauman | G06Q 20/10 705/39 |
| 2003/0105715 A1* | 6/2003 | Friedman | G06Q 20/04 705/43 |
| 2006/0111934 A1* | 5/2006 | Meggs | G06Q 20/40 705/2 |
| 2007/0112622 A1 | 5/2007 | Meggs | |
| 2007/0150355 A1 | 6/2007 | Meggs | |
| 2008/0195510 A1* | 8/2008 | Olliphant | G06Q 40/12 705/30 |
| 2009/0030801 A1 | 1/2009 | Meggs | |
| 2009/0265252 A1* | 10/2009 | Fletcher | G06Q 30/0601 705/26.1 |
| 2010/0121745 A1* | 5/2010 | Teckchandani | G06Q 20/10 705/30 |
| 2012/0173396 A1* | 7/2012 | Melby | G06Q 30/04 705/34 |
| 2013/0018777 A1* | 1/2013 | Klein | G06Q 50/01 705/38 |
| 2015/0193843 A1* | 7/2015 | Ivanoff | G16H 50/20 705/34 |
| 2017/0193477 A1* | 7/2017 | Holt | G06Q 20/102 |
| 2019/0180363 A1* | 6/2019 | Fabris | G06Q 20/14 |

* cited by examiner

VIRTUAL BILL ACCOUNT: IHS-VB872098 (MEMBER BILL)

BILL INFORMATION (61)

| PROVIDER NAME: | PROVIDER ACCOUNT: | SERVICE DATE: |
|---|---|---|
| VIERA HOSPITAL | 09-390186 | JUNE 6th, 2019 |
| BILL NUMBER | BILL TYPE: | BILL AMOUNT: |
| 897267 | BILL (POST-SERVICE) | $1,534.00 |

BILL INFORMATION (62)

| MEMBER NAME: | MEMBER ACCOUNT: | MEMBER SINCE: |
|---|---|---|
| ANTHONY MEGGS | IHS-67345 | OCTOBER, 2002 |
| PATIENT NAME: | PUBLISHED DATE: | PUBLISHED AMOUNT: |
| ARON MEGGS | JULY 23rd, 2019 | $1,534.00 |

SHARING TRANSACTIONS (63)

| MATCHED MEMBERS | | ALLOCATIONS | STATUS |
|---|---|---|---|
| BALDWIN HOUSEHOLD | (IHS 62571789) | $289.00 | SHARED |
| ASHER HOUSEHOLD | (IHS 62637823) | $198.00 | PUBLISHED |
| ZILLOW HOUSEHOLD | (IHS 62827653) | $202.00 | SHARED |
| NYQUIST HOUSEHOLD | (IHS 62982765) | $267.00 | PUBLISHED |
| SELTZ HOUSEHOLD | (IHS 62619542) | $289.00 | PUBLISHED |
| BRADLEY HOUSEHOLD | (IHS 62197823) | $289.00 | SHARED |
| | | $1,534.00 | PENDING |
| | | $780.00 | SHARED |

FIG. 4

VIRTUAL BILL ACCOUNT: IHS-VB3720987 (PRE-SERVICE ESCROW REQUEST) — 46

BILL INFORMATION — 61

| PROVIDER NAME: | PROVIDER ACCOUNT: | SERVICE DATE: |
|---|---|---|
| VIERA HOSPITAL | 09-390186 | JUNE 6th, 2019 |
| BILL NUMBER | BILL TYPE: | BILL AMOUNT: |
| 897267 | QUOTE (PRE-SERVICE) | $3,198.00 |

MEMBER INFORMATION — 62

| MEMBER NAME: | MEMBER ACCOUNT: | MEMBER SINCE: |
|---|---|---|
| ANTHONY MEGGS | IHS-67345 | OCTOBER, 2002 |
| PATIENT NAME: | PUBLISHED DATE: | PUBLISHED AMOUNT: |
| BETH MEGGS | JULY 30th, 2020 | $3,198.00 |

SHARING TRANSACTIONS — 63

| MATCHED MEMBERS | | ALLOCATIONS | STATUS |
|---|---|---|---|
| TUCKER HOUSEHOLD | (IHS 62637823) | $289.00 | SHARED |
| JEFFRIES HOUSEHOLD | (IHS 62619542) | $312.00 | PUBLISHED |
| DEMPSEY HOUSEHOLD | (IHS 62827653) | $202.00 | SHARED |
| LILLY HOUSEHOLD | (IHS 62982765) | $267.00 | PUBLISHED |
| SVITAK HOUSEHOLD | (IHS 62571789) | $407.00 | PUBLISHED |
| KANE HOUSEHOLD | (IHS 62197823) | $289.00 | SHARED |
| BALDWIN HOUSEHOLD | (IHS 62571789) | $289.00 | SHARED |
| ASHER HOUSEHOLD | (IHS 62637823) | $198.00 | PUBLISHED |
| ZILLOW HOUSEHOLD | (IHS 62827653) | $202.00 | SHARED |
| NYQUIST HOUSEHOLD | (IHS 62982765) | $165.00 | PUBLISHED |
| SELTZ HOUSEHOLD | (IHS 62619542) | $289.00 | PUBLISHED |
| BRADLEY HOUSEHOLD | (IHS 62197823) | $289.00 | SHARED |
| | | $3,198.00 | PENDING |
| | | $1,560.00 | SHARED |

FIG. 5

SHARE ACCOUNT — MEGGS HOUSEHOLD
ACCOUNT #IHS-67345

| $2,782.00 | $578.00 | $780.00 |
|---|---|---|
| TOTAL BALANCE | PENDING | RESTRICT |

RECENT ACTIVITY (LAST 30 DAYS)

| DATE | DESCRIPTION | TYPE | | |
|---|---|---|---|---|
| ⌄ PENDING TRANSACTIONS (1) | | | | |
| 7/28/2019 | MONTHLY SHARE NOTICE (AUGUST 2019) | | | |
| ⌄ POSTED TRANSACTIONS (6) | | | | |
| 7/26/2019 | MEMBER-TO-MEMBER SHARING (IHS-VB872098) | | | |
| 7/14/2019 | PROVIDER PAYMENT (IHS-VB872098) | SHARING TRANSFER (CREDIT) | ($15,587.00) | $1,424.00 |
| 7/13/2019 | MEMBER-TO-MEMBER SHARING (IHS-VB872098) | SHARING TRANSFER (CREDIT) | $15,587.00 | $17,011.00 |
| 7/3/2019 | PROGRAM SERVICES (JULY 2019) | DEBIT | ($63.00) | $1,424.00 |
| 7/3/2019 | ADMIN FEE (JULY 2019) | DEBIT | ($94.00) | $1,487.00 |
| 7/3/2019 | MONTHLY SHARE NOTICE (JULY 2019) | DEPOSIT | $578.00 | $1,581.00 |

VIRTUAL BILL ACCOUNT: IHS-VB872098 (MEMBER BILL)

BILL INFORMATION

| PROVIDER NAME: VIERA HOSPITAL | PROVIDER ACCOUNT: 09-390186 | SERVICE DATE: JUNE 6th, 2019 |
|---|---|---|
| BILL NUMBER 897267 | BILL TYPE: BILL (POST-SERVICE) | BILL AMOUNT: $1,534.00 |

BILL INFORMATION

| MEMBER NAME: ANTHONY MEGGS | MEMBER ACCOUNT: IHS-67345 | MEMBER SINCE: OCTOBER, 2002 |
|---|---|---|
| PATIENT NAME: AARON MEGGS | PUBLISHED DATE: JULY 23rd, 2019 | PUBLISHED AMOUNT: $1,534.00 |

SHARING TRANSACTIONS

| MATCHED MEMBERS | | ALLOCATIONS | STATUS |
|---|---|---|---|
| BALDWIN HOUSEHOLD | (IHS 62571789) | $289.00 | SHARED |
| ASHER HOUSEHOLD | (IHS 62637823) | $198.00 | PUBLISHED |
| ZILLOW HOUSEHOLD | (IHS 62827653) | $202.00 | SHARED |
| NYQUIST HOUSEHOLD | (IHS 62982765) | $267.00 | PUBLISHED |
| SEITZ HOUSEHOLD | (IHS 62619242) | $289.00 | PUBLISHED |
| BRADLEY HOUSEHOLD | (IHS 62192823) | $289.00 | SHARED |
| | | $1,534.00 | PENDING |
| | | $780.00 | SHARED |

FIG. 7

○ PROVIDER ACCOUNT – BALDWIN HOUSEHOLD
ACCOUNT #IHS 62571789

⤴ ACTIONS YOU CAN TAKE — 58

| $1,202.00 | $365.00 | $0.00 | $837.00 |
|---|---|---|---|
| TOTAL BALANCE | PENDING | RESTRICTED | AVAILABLE |

RECENT ACTIVITY (LAST 30 DAYS)

| DATE | DESCRIPTION | TYPE | AMOUNT | BALANCE |
|---|---|---|---|---|
| ∨ PENDING TRANSACTIONS (1) | | | | |
| 7/28/2019 | MONTHLY SHARE NOTICE (AUGUST 2019) | DEPOSIT | $365.00 | $1,202.00 |
| ∨ POSTED TRANSACTIONS (6) — 71 | | | | |
| 7/26/2019 | MEMBER-TO-MEMBER SHARING (IHS-VB8720998) | SHARING TRANSFER (CREDIT) | ($289.00) | $837.00 |
| 7/3/2019 | PROGRAM SERVICES (JULY 2019) | DEBIT | ($48.00) | $1,126.00 |
| 7/13/2019 | ADMIN FEE (JULY 2019) | DEBIT | ($63.00) | $1,174.00 |
| 7/3/2019 | MONTHLY SHARE NOTICE (JULY 2019) | DEPOSIT | $365.00 | $1,237.00 |
| 6/30/2019 | PROVIDER PAYMENT (IHS-VB8850602) | SHARING TRANSFER (DEBIT) | ($798.00) | $872.00 |
| 6/29/2019 | MEMBER-TO-MEMBER SHARING (IHS-VB8850602) | SHARING TRANSFER (CREDIT) | $798.00 | $1,670.00 |

| | | | | |
|---|---|---|---|---|
| ○ PROVIDER ACCOUNT — VIERRA HOSPITAL ACCOUNT #09-390196 | | | | ⇨ ACTIONS YOU CAN TAKE — 59 |
| $6,597.00 | | $1,534.00 | | $5,063.00 |
| BILL TOTAL | | IN PUBLISHING | | SHARED & AVAILABLE |

RECENT ACTIVITY (LAST 30 DAYS)

| DATE | DESCRIPTION | TYPE | AMOUNT | BALANCE |
|---|---|---|---|---|
| ∨ PUBLISHED TRANSACTIONS (1) | | | | |
| 7/23/2019 | PATIENT: ARON MEGGS (IHS-VB8720981) 🔗 | SHARING TRANSFER (CREDIT) | $1,534.00 | $6,597.00 |
| ∨ POSTED TRANSACTIONS (6) | | | | |
| 7/21/2019 | PATIENT: BRADLEY COOPER (IHS-VB8712891) 🔗 | SHARING TRANSFER (CREDIT) | $3,187.00 | $5,063.00 |
| 7/18/2019 | PATIENT: BART SIMPSON (IHS-VB8696721) 🔗 | SHARING TRANSFER (CREDIT) | $1,876.00 | $1,876.00 |
| 7/15/2019 | WITHDRAWAL | SHARING TRANSFER (CREDIT) | ($12,877.00) | $0.00 |
| 7/14/2019 | PATIENT: WILL SMITH (IHS-VB8671231) | SHARING TRANSFER (CREDIT) | $6,729.00 | $12,877.00 |
| 7/8/2019 | PATIENT: BILL CLINTON (IHS-VB8612891) | SHARING TRANSFER (CREDIT) | ($3,672.00) | $6,148.00 |
| 7/3/2019 | PATIENT: BILLY SUNDAY (IHS-VB8578091) | SHARING TRANSFER (CREDIT) | $1,473.00 | $2,476.00 |

FIG. 10

COMPUTING SYSTEM FOR SHARING NETWORKS PROVIDING VIRTUAL BILL ACCOUNT FEATURES AND RELATED METHODS

CROSS-REFERENCE TO RELATED APPLICATIONS

This application claims the benefit of provisional application Nos. 62/851,282; 62/851,279; 62/851,298; 62/851,395; 62/851,321 filed May 22, 2019, and provisional application No. 62/869,661 filed Jul. 2, 2019, all of which are hereby incorporated herein in their entireties by reference.

TECHNICAL FIELD

The present invention relates generally to computing systems, and more particularly, to computer infrastructures that provide for implementation of Virtual Share Exchange (VSE) platforms.

BACKGROUND

In recent years, health care expense sharing has emerged as a "decentralized" approach to financing and reserving for health care costs. As a "non-insurance" alternative, health care sharing is not subject to typical insurance regulations. Individual participants are legally and ultimately responsible for their own medical bills. However, participants in health care sharing networks willingly and consistently share from their own personal funds to pay each other's medical bills.

Some health care sharing networks implement a technology framework often called a Virtual Share Exchange (VSE). The VSE may include a collection of virtual account management, billing, and payment technologies that form a comprehensive and transparent health care sharing process. The VSE model enables health care sharing networks to facilitate sharing programs on a P2P (or member-to-member) basis to help provide compliance with applicable safe harbor exemptions to insurance regulations.

VSE platforms have enabled healthcare sharing networks to rapidly grow and scale similar to institutional computer network models, like health insurance. Modern VSE platforms have become advanced Fintech applications that integrate all the stakeholders and financial processes that are necessary to facilitate member-to-member sharing via computer networking and electronic payment infrastructure.

SUMMARY

A computing device may include a memory and a processor configured to cooperate with the memory to operate a virtual share exchange (VSE) platform by establishing member sharing accounts on the VSE platform for respective members of the VSE platform for sharing payment of member healthcare bills across a plurality of the member sharing accounts, establishing healthcare provider accounts on the VSE platform for healthcare providers issuing the member healthcare bills, and receiving member healthcare bills issued by the healthcare providers and establishing a virtual bill account on the VSE platform for each member healthcare bill submitted for payment sharing. The virtual bill account may be externally addressable through a routing number and a unique account number associated therewith. The processor may further electronically transfer funds between the sharing accounts and to the healthcare provider that issued the member healthcare bill using the externally addressable routing number and unique account number.

In accordance with one example implementation, the processor may be configured to link the virtual bill account to the sharing accounts of the member to whom the bill was issued and other members sharing in the payment of the member healthcare bill, and to the healthcare provider account of the healthcare provider that issued the member healthcare bill.

The processor may also be configured to generate graphical user interfaces (GUIs) providing access to the virtual bill account by the sharing accounts of the member to whom the bill was issued and the other members sharing in the payment of the member healthcare bill, and the healthcare provider account of the healthcare provider that issued the member healthcare bill. Additionally, the GUIs may display an aggregated sum of sharing transactions as a single sharing transfer credit to be transferred to the healthcare provider account of the healthcare provider that issued the member healthcare bill, for example. Also by way of example, the GUIs may further display all of the electronic transactions that contribute to the aggregated sum of sharing transactions.

In an example embodiment, the virtual bill accounts may be temporary, and the processor may be further configured to close the virtual bill accounts upon electronically transferring the funds to the healthcare provider that issued the member healthcare bill. In another example, the processor may be further configured to match each member healthcare bill with the sharing accounts of the other members sharing in the payment of the member healthcare bill, and allocate to each sharing account of the other members sharing in the payment of the member healthcare bill a respective payment amount to be shared for payment of the member healthcare bill. Moreover, the processor may be further configured to publish the allocated payment amounts to each of the sharing accounts of the other members sharing in the payment of the member healthcare bill during a publishing period, and electronically transferring may comprise electronically transferring after the publishing period has expired.

In some example embodiments, the processor may be further configured to receive escrow requests issued by the healthcare providers for funding prior to performing healthcare services, and establish virtual bill accounts for payment sharing for each of the escrow requests. In another example configuration, the processor may be further configured to receive loan requests for portions of the member healthcare bills not shared by the other members, allocate and publish the loan requests for repayment with interest to sharing accounts of at least some of the members of the VSE platform, and electronically transfer the loan payments and repayments between the member sharing accounts.

A related method may include establishing member sharing accounts at a server defining a VSE platform for respective members of the VSE platform for sharing payment of member healthcare bills across a plurality of the member sharing accounts, and establishing, at the server, healthcare provider accounts on the VSE platform for healthcare providers issuing the member healthcare bills. The method may further include receiving member healthcare bills issued by the healthcare providers and establishing a virtual bill account on the VSE platform for each member healthcare bill submitted for payment sharing at the server, with the virtual bill account being externally addressable through a routing number and a unique account number associated therewith. The method may also include electronically transferring funds between the sharing accounts and to the healthcare provider that issued the member healthcare bill using the externally addressable routing number and unique account number at the server.

A related non-transitory computer-readable medium is also provided for a server having a processor and having computer-executable instructions for causing the processor to perform steps. The steps may include establishing member sharing accounts defining a VSE platform for respective members of the VSE platform for sharing payment of member healthcare bills across a plurality of the member sharing accounts, and establishing healthcare provider accounts on the VSE platform for healthcare providers issuing the member healthcare bills. The steps may further include receiving member healthcare bills issued by the healthcare providers and establishing a virtual bill account on the VSE platform for each member healthcare bill submitted for payment sharing, with the virtual bill account being externally addressable through a routing number and a unique account number associated therewith, and electronically transferring funds between the sharing accounts and to the healthcare provider that issued the member healthcare bill using the externally addressable routing number and unique account number.

BRIEF DESCRIPTION OF THE DRAWINGS

FIG. 4 is a ledger view of a virtual bill account which may be provided by the VSE platform of the system of FIG. 1 in an example embodiment for a member healthcare bill.

FIG. 5 is a ledger view of a virtual bill account which may be provided by the VSE platform of the system of FIG. 1 in an example embodiment for a pre-service escrow request.

FIG. 7 is a display view of the GUI of FIG. 6 with an overlaid pop-out GUI illustrating ledger details of a virtual bill account listed in the underlying bill owner account.

FIG. 8 is a display view of a GUI generated by the computing device of FIG. 3 for a bill contributor in accordance with an example embodiment.

FIG. 9 is a display view of the GUI of FIG. 8 with an overlaid pop-out GUI illustrating ledger details of a virtual bill account listed in the underlying bill contributor account.

FIG. 10 is a display view of the GUI generated by the computing device of FIG. 3 for a bill service provider in accordance with an example embodiment.

BRIEF DESCRIPTION OF THE DRAWINGS

Example embodiments will now be described more fully hereinafter with reference to the accompanying drawings, in which the example embodiments are shown. The embodiments may, however, be implemented in many different forms and should not be construed as limited to the specific examples set forth herein. Rather, these embodiments are provided so that this disclosure will be thorough and complete. Like numbers refer to like elements throughout.

Figure 1:
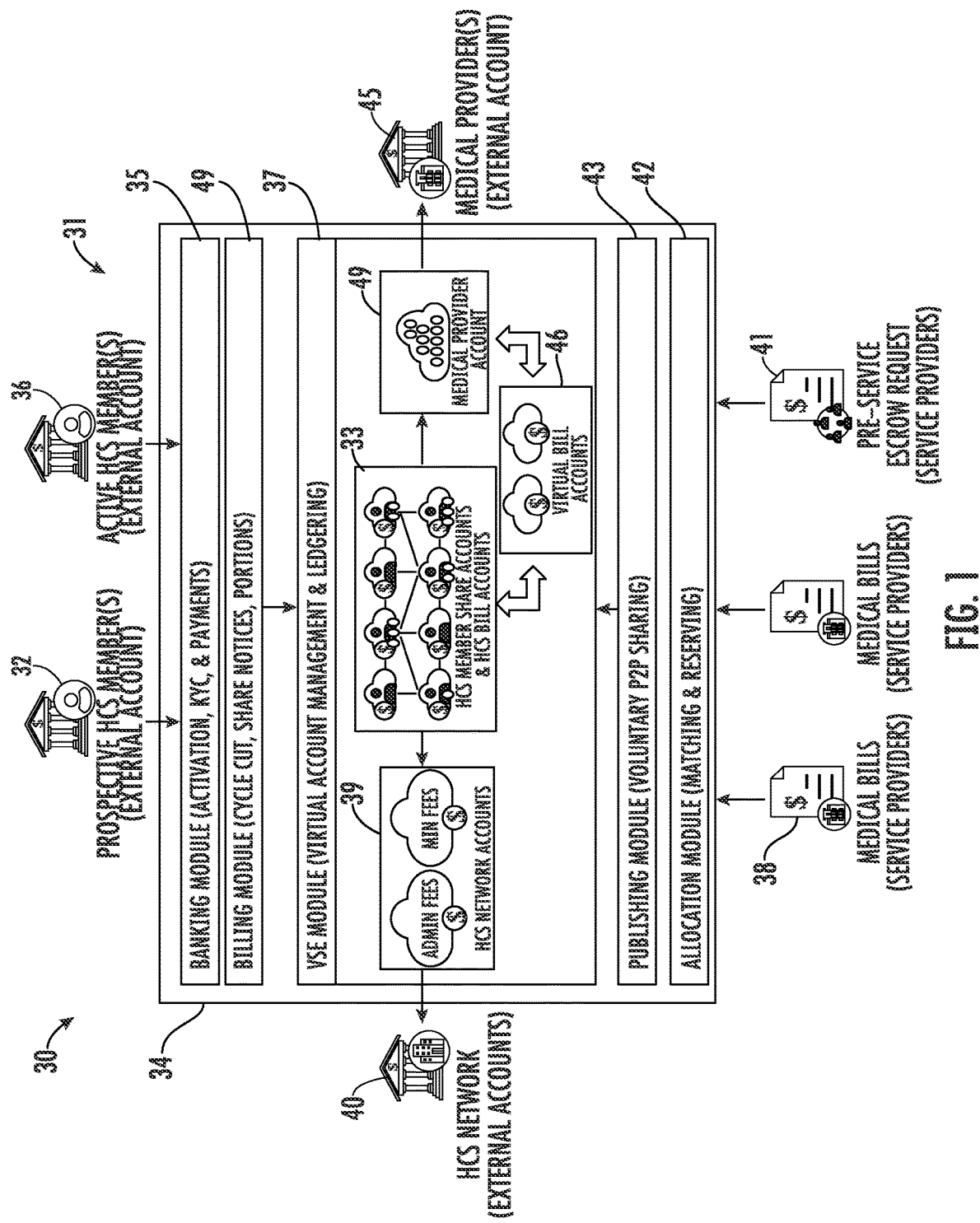
FIG. 1 is a schematic block diagram of a computing system providing virtual bill accounts within in a virtual share exchange (VSE) network platform in accordance with an example embodiment.
Figure 2:
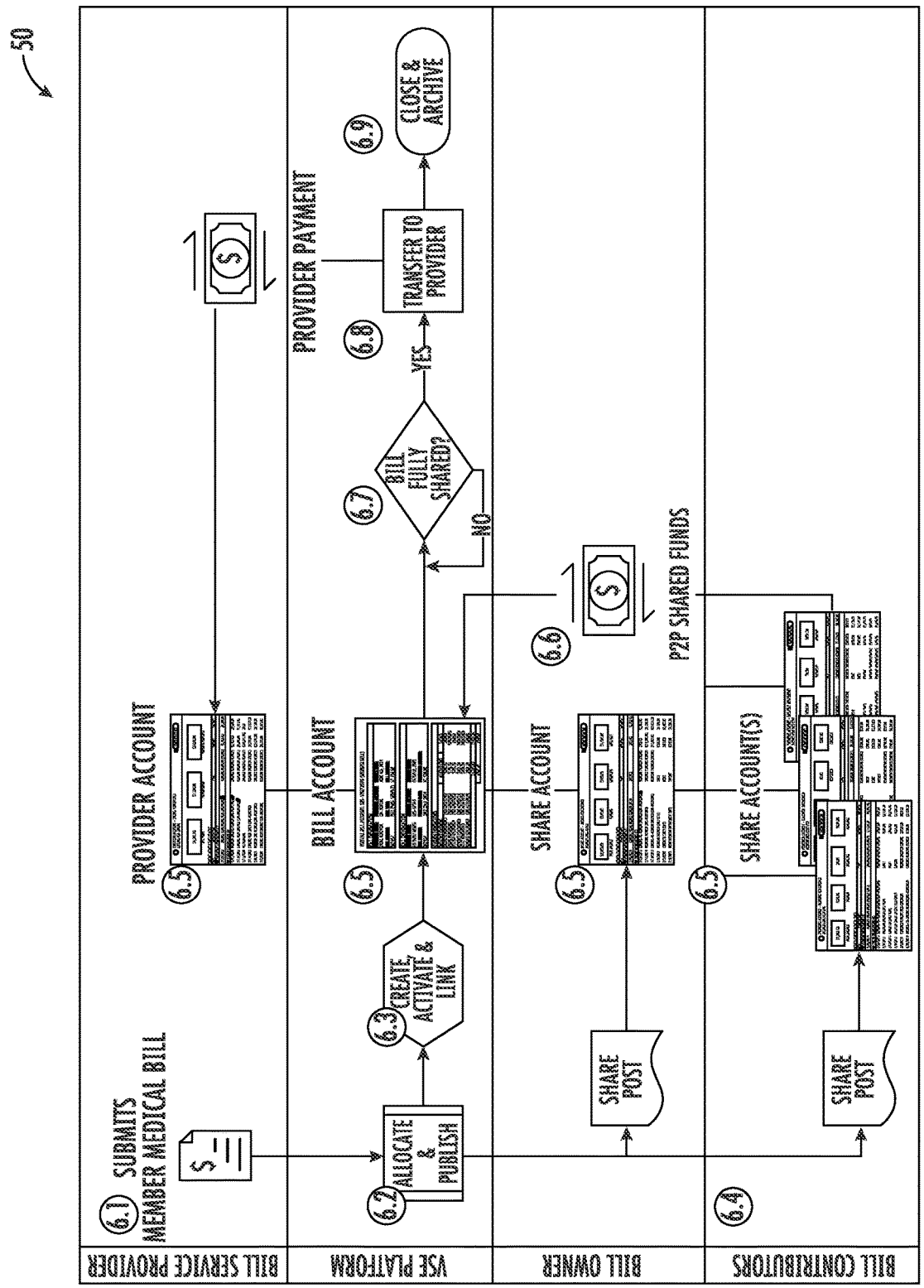
FIG. 2 is a sequence flow diagram illustrating example method aspects associated with the system of FIG. 1.

Referring initially to FIGS. 1-2, a computing system 30 which advantageously provide for the generation of virtual bill accounts to link payment sharing sources with the service provides in a manner that allows for accessibility and electronic fund transfers as if the virtual bill account was a stand-alone bank account, yet this may be done in an automated fashion and "on the fly" as member healthcare bills are received. The system 30 may advantageously be used to implement a virtual share exchange (VSE) network platform 31. By way of background, individuals joining forces as a group to achieve certain benefits and advantages is common in many facets of our everyday life. The power of groups is largely evident in the pooling practice found in the traditional insurance model. By pooling their resources through a centralized insurance company or common fund, groups are able to finance, reserve, and pay the expenses associated with the type of insurance risk. Without being able to rely on the insurance company and its practice of pooling funds, the individuals would be left to bear the cost and risk of a catastrophic loss by themselves.

Historically, traditional insurance companies were largely successful at helping groups of individuals finance and reserve for their expenses and catastrophic risk. By collecting and pooling both the risk and the resources of individuals into centralized group fund, traditional insurance coverage and the benefits obtained therefrom were made more affordable. In the past, the efficiency of pooling and reserving resources in a centralized fund enabled insurance companies to not only provide affordable coverage, but to capture a profit or bounty for pooling those resources into a central fund. Resources that are collected and pooled into the centralized fund are called "premiums", which is derived from the Latin word "praemium" and defined as a "reward, profit or bounty for a specified act". Thus, insurance companies were able to generate significant profit by extracting a "premium" from groups of individuals who were unable to pool resources to finance and reserve for their individual risk of catastrophic loss and costs.

Traditionally, the affordability of insurance coverage was predicated upon the overall wellness of the group and their consumption of services. For example, in healthcare, some members' need for medical services could be little more than annual checkups, while other individuals might need to access and consume services much more extensively. It is the latter group that has a greater effect on the overall costs of the group and the subsequent premiums collected. For those that do not frequently draw upon the centralized fund's resources, being lumped with the more extensive users is unfavorable. On the flip side, those who consume a larger share of the benefits may enjoy lower premiums because the individuals that consume little are subsidizing the expense of frequent consumers. In the past, insurance companies would respond to individuals who draw disproportionally on the centralized fund by raising their premiums to maintain group equity and ensure company profits.

With respect to financing and reserving for health care, the average consumer would not be able to afford much more than the very basic of health care services if the pooling of resources was not available through insurance. In fact, based upon current rates being charged by the medical industry, cutting edge or life-saving surgeries, drugs and treatments would be difficult, if not, impossible, for the average consumer to obtain.

However, in recent years the affordability and profitability of the traditional insurance model has been degraded by the enactment of government regulations. New laws and regulations have all but eliminated an insurance company's ability to segment groups of healthy individuals into centralized funds, or plans, that price premiums according to the group's health and draw on resources. Similarly, new regulations have mandated that all centralized funds, or plans, cover new and more extensive medical services not historically offered by health insurance companies. As a result, health insurance companies have been greatly limited in their ability to offer affordable coverage that is reflective of the health condition and medical usage of individual participants, as well offer affordable plans that provide access to the medical services that participants actually desire, versus services the government mandates.

Another disadvantage of the health insurance model and the associated regulations is that individuals of the centralized fund and plan can lead unhealthy or "at risk" lifestyles such as high-risk diets, low exercise, smoking, excessive alcohol intake and the use of illicit drugs, all without consequence. By engaging in such lifestyles, these individuals increase their likelihood of drawing on the resources and benefits of the centralized fund. The more these "high-risk" individuals are allowed to make choices and lead lives without consequences, the more likely that costs and premiums increase for everyone in the fund.

An additional disadvantage of the centralized insurance model is that the plan benefits are distributed to individuals of the group in such a way that no other individual participating in the plan has any real sense of what types of benefits or services are being paid for by the insurance company. The centralized insurance model provides no visibility into the size of the fund, the number of participating individuals, the size of available reserves, the flows of money, or profits pocketed by the insurance company. Thus, participating individuals are unaware of the financial health and wellness of the fund. This lack of transparency also makes individuals feel less responsible for their lifestyle choices that increase their draw of resources, as well as less connected and accountable to their fellow participants who are paying their bills.

The structural inefficiencies, inherent in the design of the centralized health insurance model, have been recently exposed by the new government mandates and regulations in health care. It has caused a rapid and unsustainable rise in premiums and insurance costs. Thus, the centralized health insurance model has become unaffordable and subsequently obsolete. And while the changes have been focused exclusively on healthcare, the aforementioned problems similarly persist in the other insurance markets.

As a result, consumers have sought out new and more innovative ways to organize themselves into groups that leverage the strength of their combined resources to finance and reserve for their health care costs. Unlike the centralized insurance model, consumers are turning to decentralized network models that are enabled by technologies that replace the pooling functions of traditional insurance companies.

In recent years, health care sharing has emerged as the most popular "decentralized" approach to financing and reserving for health care costs. As a "non-insurance" concept, health care sharing is not encumbered by insurance regulations. Individual participants are legally and ultimately responsible for their own medical bills. However, participants in health care sharing networks willingly and consistently share from their own personal funds to pay each other's medical bills. Health care sharing networks have been in existence since the early 1980s, but in recent years have grown to become a significant alternative to the centralized insurance model. Today, health care sharing networks enjoy safe harbor exemptions in U.S. health care laws and more than thirty states. Participants of health care sharing networks are sharing billions of dollars' worth of medical bills on an annual basis. Free from insurance regulations, health care sharing networks can design and implement programs that are more efficient and affordable than insurance, as well as hold participants more accountable to each other.

As noted above, some health care sharing networks implement a technology framework often called a Virtual Share Exchange or VSE. The VSE may include a collection of computing hardware (e.g., servers or other computing devices including microprocessors and associated memory with non-transitory computer readable instructions) to implement virtual account management, billing, and payment modules that form a comprehensive and transparent health care sharing process. The VSE model enables health care sharing networks to facilitate sharing programs on a P2P (or member-to-member) basis to help ensure that these sharing networks refrain from the practice of insurance, and remain in compliance with the safe harbor exemptions of insurance rules/regulations.

Referring initially to FIG. 1, a VSE platform 31 in accordance with an example embodiment is first described. In general, VSE platforms have enabled healthcare sharing networks to rapidly grow and scale their networks by leveraging social trends towards the democratization of centralized institutional business models, similar to health insurance. The VSE platform 31 provides advanced Fintech applications that integrate all the stakeholders and financial processes that facilitate member-to-member sharing of, in the present example, member healthcare bills.

More particularly, prospective members 32 are consumers who are applying for membership into the sharing network and its community. In order to complete their application for membership, prospective members 32 set up and activate their share account 33 through a computing device(s) 34, such as a server. In an example embodiment, the computing device 34 may be part of a cloud computing architecture, although other configurations may be used in different embodiments. Share accounts 33 are activated through a graphical user interface or GUI (often called the Application Center or Activation Center) to access account activation services within a banking module 35 of the computing device 34.

Active members 36 are consumers who have been accepted and are active in the sharing network and associated community. Active members 36 make monthly deposits (called monthly share amounts) electronically into their share account 33 that is held within a VSE/for the benefit of (FBO) module 37 of the computing device 34. To pay (or deposit) their monthly share amount into their share account 33, members 36 access services within the banking module 35 through a graphical user interface, as will be discussed further below. The banking module 35 provides services that enable members 36 to link their share account 33 to an external payment method and initiate recurring monthly transactions.

The banking module 35 may be implemented as a cloud-based application that enables both prospective members 32 and active members 36 to activate and manage their participation in the sharing network's program through a financial account (called a share account 33) that the member owns and controls. The banking module 35 enables members 36 to link an external bank account to their share account 33, to fund their share account per the terms of the sharing network, and to manage banking and regulatory compliance.

The billing module 49 may be implemented as a cloud-based application that calculates monthly share prices and creates the monthly share notices for the sharing network. Moreover, the billing module 49 bills, publishes and collects the monthly share notice per the terms of the sharing network.

The VSE/FBO module 37 may also be implemented as a cloud based virtual account management and ledgering system that enables the sharing network to facilitate the member-to-member sharing and payment of member bills. The VSE/FBO module 37 enables member-to-member sharing through virtual accounts 33 that are owned and individually controlled by the members 36 and not the sharing network, as well as to house those virtual accounts in a single FBO account held by a financial institution "for the benefit of" the member 36.

The member share accounts 33 are member owned and controlled virtual accounts maintained by the VSE/FBO module 37, and are required for members 36 to participate in the sharing network. The share accounts 33 enable the sharing network to build distributed reserves in accounts that are owned and controlled by its members 36, and facilitate member-to-member sharing through those accounts.

Sharing network fee accounts 39 are virtual accounts maintained by the VSE/FBO module 37 that are owned and controlled by the sharing network and used to comply with any potential regulatory constraints. The fee accounts 39 help segregate "member owned" funds that are held in share accounts 33 and used for sharing from "network owned" funds, which are operating fees that are billed and collected as a part of a monthly share notice.

Sharing network external accounts 40 are external bank accounts that are owned and controlled by the sharing network and are linked to a specific sharing network fee account 39 that resides in the VSE/FBO module 37. As operating fees are collected through the payment by members 36 of monthly share notices, the sharing network is able to access those funds by transferring them out of the sharing network fee account 39 to its linked external account 40. The sharing network external accounts 40 allow for withdrawing operating funds out of the VSE/FBO module 37.

The member bills 38 are invoices billed by a member's service provider that have been received by the sharing network. The member bills 38 are to be shared by the members of the sharing network per the network's guidelines. In some instances, medical providers might also submit a pre-service escrow request 41 to request a pre-payment or escrow of funds before services are rendered, as will be discussed further below.

An allocation module 42 may be implemented as a cloud-based bill matching and allocation service enabling the sharing network to facilitate bill sharing, help ensure regulatory compliance, and to generate more meaningful sharing transactions. The allocation module 42 may be used to match and allocate bills on a member-to-member basis, and to draw down distributed bills in a way that is equitable to all members 36.

A publishing module 43 may be implemented as a cloud-based notification and sharing service for initiating member-to-member (or P2P) account transfers. The publishing module 43 notifies members 36 as to whose bill they have been matched to, and how much of their available share account 33 balance has been allocated as a contribution to the payment that member's bill, as well as to provide each matched member with the means to voluntarily share (agree) in the payment of that bill.

The provider account 44 is a virtual account within the VSE module 37 that is owned and managed by individual service providers, or a single virtual "settlement" account that aggregates funds for multiple payments made to multiple service providers, or some combination of both. The provider account(s) 44 segregate funds that have been shared and collected for the payment of a bill 38 or 41, and to make those funds available to the appropriate service provider.

An external provider account 45 is a linked external account owned and managed by an individual service provider for transferring funds out of the VSE/FBO module 37 or linked external account owned and managed by a payment processor for transferring multiple payments to be made to multiple service providers. More particularly, the provider external accounts 45 allow for withdrawing bill payments out of the VSE/FBO module 37.

Despite the rapid growth of sharing networks, especially healthcare sharing networks, healthcare sharing networks have traditionally not had the technical ability to incorporate medical providers within the sharing network environment. However, the VSE platform 31 advantageously allows for medical providers to be incorporated into the process of healthcare sharing through the use of virtual bill accounts 46 implemented by the VSE module 37 to enhance provider visibility and remit payments for bills in a manner that is more efficient for the provider community.

More particularly, the VSE platform 31 equips medical providers, and other potential stakeholders, to actively participate in the process of healthcare sharing, as well as provide greater transparency into the sharing transactions related to a member's medical bills. Generally speaking, the medical provider community has been cautious to embrace a concept where the payor is not an insurance company or the patient making a cash payment. Other than the care that they provide to their patients, a medical provider's primary concern is to make certain that they get paid for the care provided. Whereas, insurance companies are obligated to pay providers per the terms of a contract or a "cash pay patient" can be required to pay by credit card or payment terms before services are rendered, medical providers maybe more cautious of placing trust in a healthcare sharing network and its members to remit payment for a patient's bill.

While the movement of patients (i.e., members 36) towards healthcare sharing has not been slowed by provider caution, sharing networks may further benefit when providers are assured of a network's "ability to pay" their patient's medical bill by gaining access and visibility into the sharing process. As healthcare sharing continues to grow and the provider community will engage and serve even larger numbers of members, they are more likely to embrace sharing networks who provide transparency and demonstrate the intent and ability to pay member bills.

Thus, the VSE platform 31 advantageously provides a computing architecture that incorporates medical providers into the sharing process of their patient's bills within the sharing network. The approach described herein may replace the process of member-to-member (or P2P) sharing that is practiced in earlier generations of VSEs. Where earlier generations facilitated P2P sharing through direct transfers between member share accounts, the VSE platform 31 implements P2P sharing through virtual bill accounts 46 that are uniquely linked to (1) the member share account of the bill owner, (2) the member share accounts of bill contributors, and (3) the provider account of the bill service provider who submitted the bill. For example, the virtual bill accounts 46 may be established within a database architecture in which the unique IDs of members 36 and/or member accounts 33 are linked to a unique table that is created on the fly to define the virtual bill account responsive to the submission of a medical bill 38 to be funded.

The use of virtual bill accounts 46 enables sharing networks to integrate and engage any number of stakeholders associated with the payment of a member bill or obligation. A virtual bill account is a single purpose virtual account and ledger within the VSE/FBO Module 37 that is created for a specific purpose and is linked to those members of the network, and third parties, who have an interest in the purpose of the newly created account. Transactions in the virtual bill account 46 are made viewable to some or all stakeholders who hold their own accounts within the VSE/FBO Module 37. Funds in the virtual bill account 46 are restricted (unavailable) until the single purpose of the account has been completed and funds are released to the intended stakeholder.

In the case of the VSE platform 31 supporting a healthcare sharing network, a virtual bill account 46 is a temporary account that is opened when the VSE platform receives a member medical bill 38 and then matches, allocates and publishes the bill for sharing. The virtual bill account 46 is linked at least to the member share accounts 33 of the bill owner and bill contributors. The medical provider that submitted the bill is a stakeholder in the sharing process and gains access by establishing a provider account 44 on the VSE platform 31. Other potential stakeholders might be P2P lenders (members), or third-party lenders who desire to assist members in paying bills not shared by the network, for example. The virtual bill account 46 is not a sub-account of any one stakeholder. Rather, the virtual bill account 46 is a temporary single purpose account that is linked to potentially multiple stakeholders. Funds collected in a virtual bill account 46 are restricted and unavailable dollars, but can be displayed as "pending" (unsettled) transactions in more than one stakeholder's account.

Thus, sharing networks can invite and engage medical providers into the sharing process by providing them with a provider account 44 that displays both a pending and available balance and sums the active amount of their patient bills submitted to the network. The "pending" balance is restricted and represents the total patient bill amounts that are in the process of being published, shared and transferred to their respective virtual bill account 46. The "shared and available" balance is unrestricted and represents the total patient bill amounts that have been shared in a virtual bill account and can now be withdrawn by the Provider.

Virtual bill accounts 46 are equipped with a linking feature that enables sharing networks to uniquely display numerous sharing transactions related to a member medical bill 38 as a single sharing transaction in the member share accounts 33 of the bill owner, bill contributors and bill service provider. For example, Bob's bill for a $50,000 knee replacement surgery gets matched, allocated, published and shared by 200 members who contributed $250.00 each. The 200 transactions can be displayed in Bob's share account 33 as a single $50,000 "restricted" credit. If Bob desires, he can click on the $50,000 transaction in his GUI to display the virtual bill account 46 and have it display the names and amounts that each member contributed, as will be discussed further below. Likewise, the provider account of Bob's surgeon can display a $50,000 "pending" credit in his provider account 44 until all monies are settled and can be electronically transferred to Bob's surgeon's bank account. Like Bob, the surgeon can click on the $50,000 transaction in his GUI to display the virtual bill account 46 member contributions as well.

Virtual bill accounts 46 may accordingly provide enhanced flexibility, transparency, and security. Moreover, levering the capabilities of virtual bill accounts 46 will enable new VSE features that will be embraced by providers, such as provider direct payments and P2P loan requests, where members assist each other in paying bills that are ineligible for sharing, as will be discussed further below.

The virtual bill accounts 46 may be dynamically activated and deactivated by the VSE platform 31 for the purpose of sharing and paying a given member medical bill 38 by coordinating the sharing transactions between the bill member and bill contributors, and the transfer of payment to the bill service provider. The VSE platform 31 integrates several technical advantages in the computing system 30. For example, as an Evolution of P2P Sharing (Member-to-Member), the virtual bill accounts 46 provide an automated approach enabling sharing networks to facilitate P2P sharing transactions. This is important for healthcare sharing networks that are required by many states to voluntarily share funds from member-to-member. More particularly, first generation of VSE platforms enabled P2P sharing by moving funds member-to-member through the use of physical bank accounts or notional accounts inside of a custodial/escrow structure. That is, first generation P2P sharing consisted of matching and allocating funds held in the share accounts of a bill contributor, and then moving those funds directly to the share account of the bill owner.

On the other hand, the virtual bill accounts 46 advantageously allow for the replacement of direct transfers between member share accounts with the use of single purpose accounts that are automatically spawned and closed by the VSE module 37 on demand. That is, the VSE module 37 dynamically creates and activates single purpose virtual bill accounts 46 to coordinate sharing transactions for a specific medical bill 38. In this approach, P2P sharing is facilitated through a virtual bill account 46 that is dynamically activated by the VSE module 37 whenever a bill is allocated and published for sharing, and then deactivated when the bill has been shared and resolved.

The VSE platform 31 equips sharing networks to dynamically create a virtual bill account 46 whenever a specific medical bill is allocated for sharing. The virtual bill account 46 is created to coordinate sharing for a specific medical bill 33. The virtual bill account 46 is linked to the accounts 33 of the bill owner and the bill contributor(s), and optionally to the account 44 of the service provider as well. The virtual bill account 46 is used to collect funds from a bill contributor who has been matched to share in the specific bill for which it was created. The use of virtual bill accounts 46 is a contemporary Fintech approach to voluntary member-to-member sharing. The virtual bill account 46 enables member-to-member sharing transactions for large medical bills that can span hundreds of bill contributor accounts 33 (or more) by providing a detailed and auditable ledger of all related sharing transactions.

As noted above, first generation P2P sharing was executed through VSE platforms that used physical bank accounts as member share accounts. In some instances, notional accounts inside of a custodial/escrow structure were used as share accounts. In both scenarios, sharing transactions moved directly from one member's share account to another member's share account. However, physical bank accounts or notional accounts created technical challenges that virtual bill accounts 46 resolve. Sharing through physical bank accounts, for a community of hundreds of thousands of members (or more) can be extremely expensive, complex and cumbersome.

Sharing through notional sub-accounts within an escrow structure is less expensive, less complex and more manageable for large communities. However, notional sub-accounts are not addressable and do not provide sharing networks with the ability to draw checks or Automated Clearing House (ACH) transactions against the share accounts (i.e., notional sub-accounts). An additional concern is the fact that notional sub-accounts that serve as member share accounts cannot be managed or controlled by the member. Thus, sub-accounts might fall short of a regulator's strict definition of voluntary member-to-member sharing.

Virtual bill accounts 46 are relatively inexpensive to implement and relatively easy to manage and use, plus they are addressable. More particularly, each virtual bill account 46 has an externally addressable routing and account number from which checks and ACH transactions can be drawn. The VSE platform 31 accordingly may incorporate recent Fintech developments in virtual account management and ledgering to facilitate a more advanced form of healthcare sharing. In the VSE platform 31, all accounts that are created and activated within the VSE module 37 enjoy the benefits of a physical bank account. Member share accounts 33, provider accounts 44 and virtual bill accounts 46 all reside within the VSE/FBO Module 37, which may be implemented within a single physical bank account held by a financial institution. The FBO account at the financial institution is held and titled "for the benefit of" the sharing network's members 36. All account transactions within the VSE/FBO account are "on us" transactions and are simple to initiate and manage, and may be done for relatively little or no cost.

This VSE platform enables the automated creation, activation and deactivation of numerous addressable single purpose virtual bill accounts 46 for each medical bill 38 submitted to the sharing network. This advantageously allows a healthcare sharing network with the ability to create a virtual account and ledger for every unique medical bill published and shared by the community. Moreover, each virtual bill account 46 within the VSE/FBO module 37 is externally addressable with a routing number and account number, as noted above. This enables the VSE module 37 with the ability to coordinate and ledger sharing transactions between bill owners and bill contributors and then, through the use of the addressable account number, transfer funds as payment to the provider account 44 that resides inside of the VSE module, or another account that reside outside of the VSE module in a physical bank account with any bank. This enables the ledgering and full reconciliation from the beginning point of publishing a bill for sharing to the end point of paying a provider who exists inside or outside of the sharing system.

The virtual bill accounts 46 are single purpose accounts that are dynamically created and activated within the VSE/FBO module 37 for a specific purpose (which, in the present example, is paying a given medical bill 38), and thereafter they are deactivated and archived whenever that specific purpose is complete. This process will now be described further with reference to the sequence flow diagram 50 of FIG. 2.

The bill service provider (medical provider) submits the member's medical bill 38 to the sharing network for payment, at step 6.1. Next, the VSE module 37 matches, allocates and publishes the member's medical bill to the network's members 36 for sharing, at step 6.2. The VSE module 37 further dynamically creates and activates a single purpose virtual bill account 46 for coordinating the sharing, collection and payment of the member medical bill, at step 6.3. The VSE module 37 may further send a notification called a share post (step 6.4) to both the bill owner and the bill contributor(s). The bill owner is notified that their bill has been published for sharing, as well as the name of and amount that each bill contributor will contribute. The bill contributors are notified as to whose bill they have been matched with, and the amount that they have been allocated to contribute.

The VSE module 37 links the share accounts 33 (step 6.5) of the bill owner and the bill contributors to the virtual bill account 46, as well as the provider account 44 of the bill service provider (step 6.5). Moreover, the VSE module 37 transfers funds (step 6.6), after the publishing period has ended, from the share accounts 33 of the bill contributors to the virtual bill account 46 for the single purpose of sharing and paying the given member medical bill 38.

The VSE module 37 monitors all sharing transactions and collections (step 6.7) in the virtual bill account 46. The virtual bill account 46 remains open and active until sharing transactions, equal to the published amount, have been received. Once the member medical bill 38 is fully funded, the VSE module 37 transfers the balance (step 6.8) of the virtual bill account to the provider account 44 (or outside of the VSE module) as the network's approved payment for that bill. Once all funds have been transferred to the provider's account, the VSE module 37 automatically deactivates and archives the virtual bill account 46 (step 6.9) with detailed member-to-member sharing transactions for the bill.

The virtual bill accounts 46 act as an auditable ledger for a multi-stakeholder transaction that extends over a period of time. As previously noted, a virtual bill account 46 serves as the ledger of multi-party transactions related to a single purpose for which it was created, and it is temporary in that it is not a perpetual account. The virtual bill account 46 has a "beginning and end" of the purpose for which it was created. In the case of healthcare sharing, a virtual bill account 46 can be used to register transactions for multiple purposes across multiple stakeholders related to the sharing network and its community.

Virtual bill accounts 46 may be used to share pre-service invoices or escrow requests 41, as well as post-service bills 38. In the case of a post-service bill 38, the virtual bill account 46 serves as a ledger for the single purpose of coordinating and registering all sharing transactions for a "post-service" bill (FIG. 5), and then coordinating and registering the transfer of the account balance to a provider account 44 as payment to the medical provider for a fully funded medical bill. Serving as the ledger for sharing transactions related to a specific post-service bill 38 may typically be the primary use of virtual bill accounts.

However, in certain instances sharing of a pre-service member bill (escrow request) 41 may also be appropriate. In the example of FIG. 5, a virtual bill account 46 serves as a ledger for the purpose of coordinating and registering sharing transactions for a pre-service bill 41, or what might otherwise be considered as a quote for medical services. In some instances, medical providers might require a pre-payment or escrow of funds before services are rendered. This is especially true with large bills. The VSE module 37 may advantageously be configured to facilitate pre-payment terms by publishing a quoted amount and then registering the sharing transfer of funds into a virtual bill account 46 that is linked to the provider account and made visible to the provider that is providing care. Once proof of services rendered has been obtained to the satisfaction of the sharing network, funds that are being held (escrowed) are released and transferred to the provider account 44.

Still another use for the virtual bill accounts is for enabling P2P "micro" loans for paying member responsibilities. More particularly, a virtual bill account 46 can serve as a ledger for coordinating and registering loan and repayment transactions related to a P2P loan from network members that is needed to pay a specific member medical bill. It is typically the case in healthcare sharing that a member is often required to pay a first-dollar portion of an eligible medical bill. This is most likely to be in the form of a deductible or a co-share amount. There are also times when all or a portion of the medical bill is ineligible to be shared by the members. This usually takes the form of ineligible procedures or caps on eligible procedures. In both scenarios, members are often in need of a lending source in order to pay these amounts, which are often referred to as the member responsibility amount. The member responsibility amounts are not shared by the other members 36. Just as an eligible bill amount can be matched, allocated and published to members by the VSE module 37, so too can a loan request be matched, allocated and published to multiple members 36 willing to lend a portion (a micro-loan) of the loan request to the member for a profit. Because of the unique account linking properties of a virtual bill account 46, they are well suited for maintaining a ledger of P2P micro-loans related to the member responsibility amount for a particular bill 38.

Another advantageous feature of the virtual bill accounts 46 is that they can be linked to the virtual accounts of stakeholders who hold interest in the purpose for which the account was created. To engage and benefit from this account linking feature, stakeholders open and maintain their own virtual accounts within the VSE system.

In the case of healthcare sharing, to engage the medical provider community and invite them into the sharing network, medical providers may create and activate their own provider accounts 44 in the VSE platform 31 to enjoy the full benefits and features of virtual bill accounts 46. Providers may open accounts with individual sharing networks, or open an account with a Payment service that integrates with the VSE platforms 31 of multiple networks. In doing so, medical providers can gain access and visibility into the status and progress of their patient bills, as well as gain access to their patient payments as soon as those bills are shared.

Figure 3:
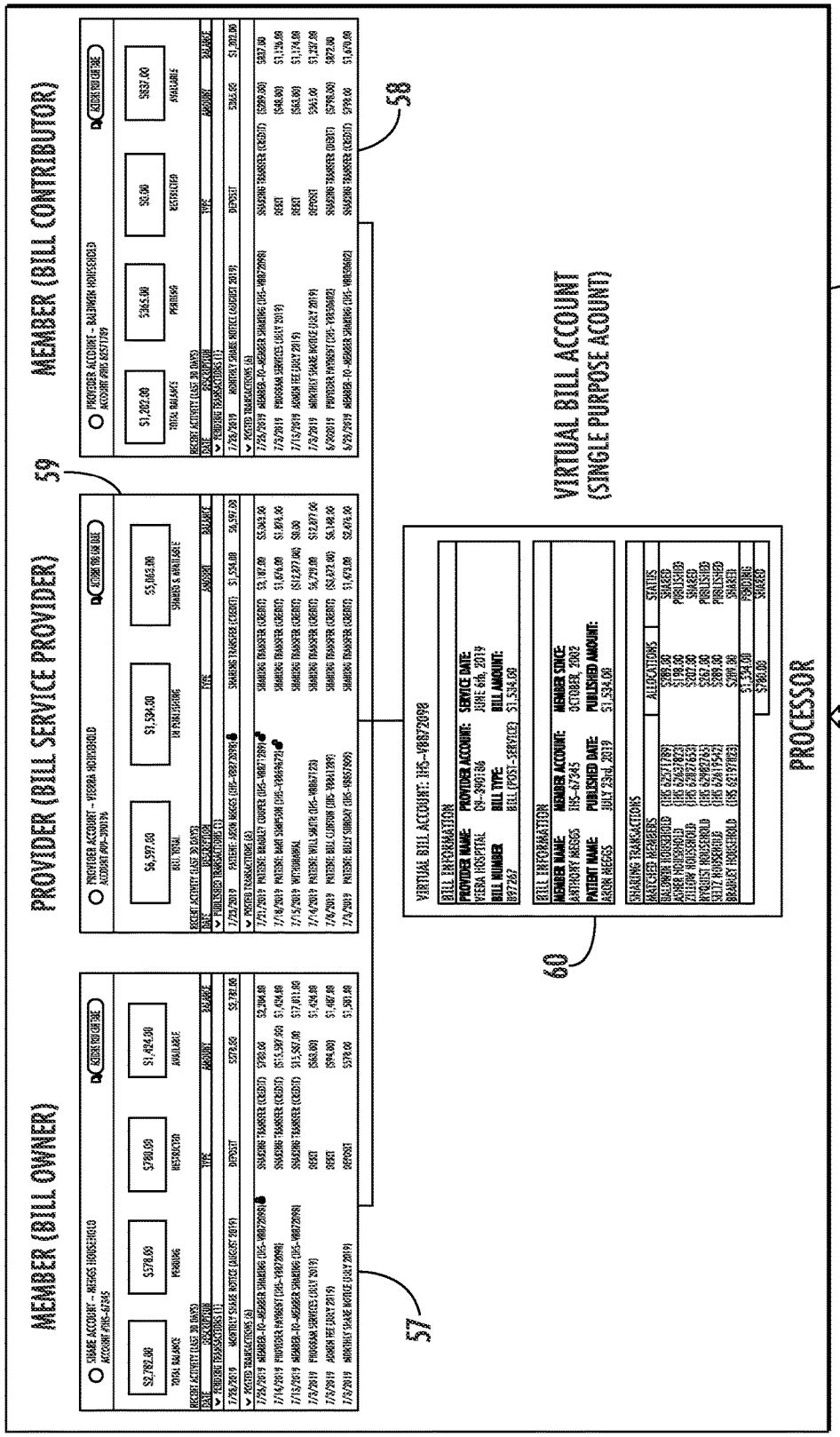
FIG. 3 is a schematic block diagram of a computing device of the system of FIG. 1 which may be used to implement the VSE platform thereof in an example embodiment.

In the example of FIG. 3, the server 34 illustratively includes a memory 55 storing non-transitory computer executable instructions, and an associated processor 56 which cooperates with the memory to operate the VSE platform modules 35, 37, 42-43, 49, and perform the associated steps described herein based upon the stored instructions. In the illustrated example, the processor 56 generates respective graphical user interfaces (GUIs) 57, 58, 59 for the bill owner, bill contributor, and bill service provider. Moreover, the processor 56 also generates a GUI for displaying the virtual bill account 46 ledger information, which is accessible by all of the bill owner, bill contributors, and bill service providers.

Whenever the VSE platform 31 creates and activates a virtual bill account 46 to coordinate P2P sharing transactions, it links the virtual bill account to the share account 33 of the member 36 who is the bill owner and the share account of the member(s) who has been matched and allocated as bill contributor(s). In the illustrated example, the virtual bill account is not a sub-account of any account 33, 44 held by the bill owner, bill contributor, or bill service provider. The virtual bill account 46 is instead a linked account, in that it is an addressable virtual account held in the VSE/FBO module 37 for the single purpose of sharing and funding the given bill 38 (or pre-service request 41).

The account linking feature of virtual bill accounts 46 may advantageously enable a desired level of visibility, transparency, accountability and flexibility into the P2P sharing process not yet achieved with prior VSE configurations. Linking virtual bill accounts 46 to stakeholder accounts 33 enables sharing networks to engage bill service providers into a linear sharing and payment process that spans time. Virtual bill accounts 46 engage bill service providers by enabling sharing networks to display their patient bills and the state of sharing progress as pending transactions in their provider accounts 44. This is especially useful in the healthcare sharing context, as medical providers can watch their patient bills 38 be submitted, matched, allocated, published, shared and paid by the sharing network and its community of members.

The virtual bill accounts 46 also enable a multi-transactional view into a P2P sharing process that can span time and multiple stakeholders. Linking a virtual bill account 46 to its related stakeholders enables a sharing network to build stakeholder account views that display "pending" or "in progress" transactions that provide transparency into the process.

In the present example of healthcare sharing, linking the share accounts 33 of bill owners and bill contributors to virtual bill accounts 46 enables sharing networks to create share account views through GUIs 57-60 that bring enhanced visibility and transparency to healthcare sharing. In the example of FIG. 4, a temporary virtual bill account 46 has been created and activated by the VSE platform 31 for the purpose of coordinating sharing transactions for a specific member bill 38. The member information section 62 indicates that a bill of $1,534.00 has been received, matched, allocated and published by the VSE platform 31 to be shared by network members. The network member is Anthony Meggs and the bill is for Aron Meggs who is a member of the Meggs household. The virtual bill account 46 has been linked to Anthony Meggs (the bill owner) as indicated by the member account number.

The sharing transactions section 63 indicates that (6) six member households have been matched to share in the Meggs medical bill 38 and they have each been allocated a certain amount to be transferred (debited) out of their share accounts and credited to the share account of the bill owner (Meggs). This section also indicates the progress status of each individual allocation. Thus far, $780.00 have been transferred from the share accounts of three bill contributors, settled in the virtual bill account 46, and credited to the share account of the bill owner (Meggs). The remaining three allocations are still in the "published" status. The share accounts of all six contributors have been linked to the virtual share account 46, as indicated by member account numbers displayed with each allocation. As will be discussed further below, bill information section 61 indicates that the medical bill was submitted by Viera Hospital (the bill service provider), and the provider account 44 of the bill service provider has been linked to the virtual bill account 46, as indicated by the provider account number. So, in the present example, the virtual bill account 46 has been linked to eight different stakeholders, namely the bill owner (1), bill contributors (6), and bill service provider (1).

Figure 6:
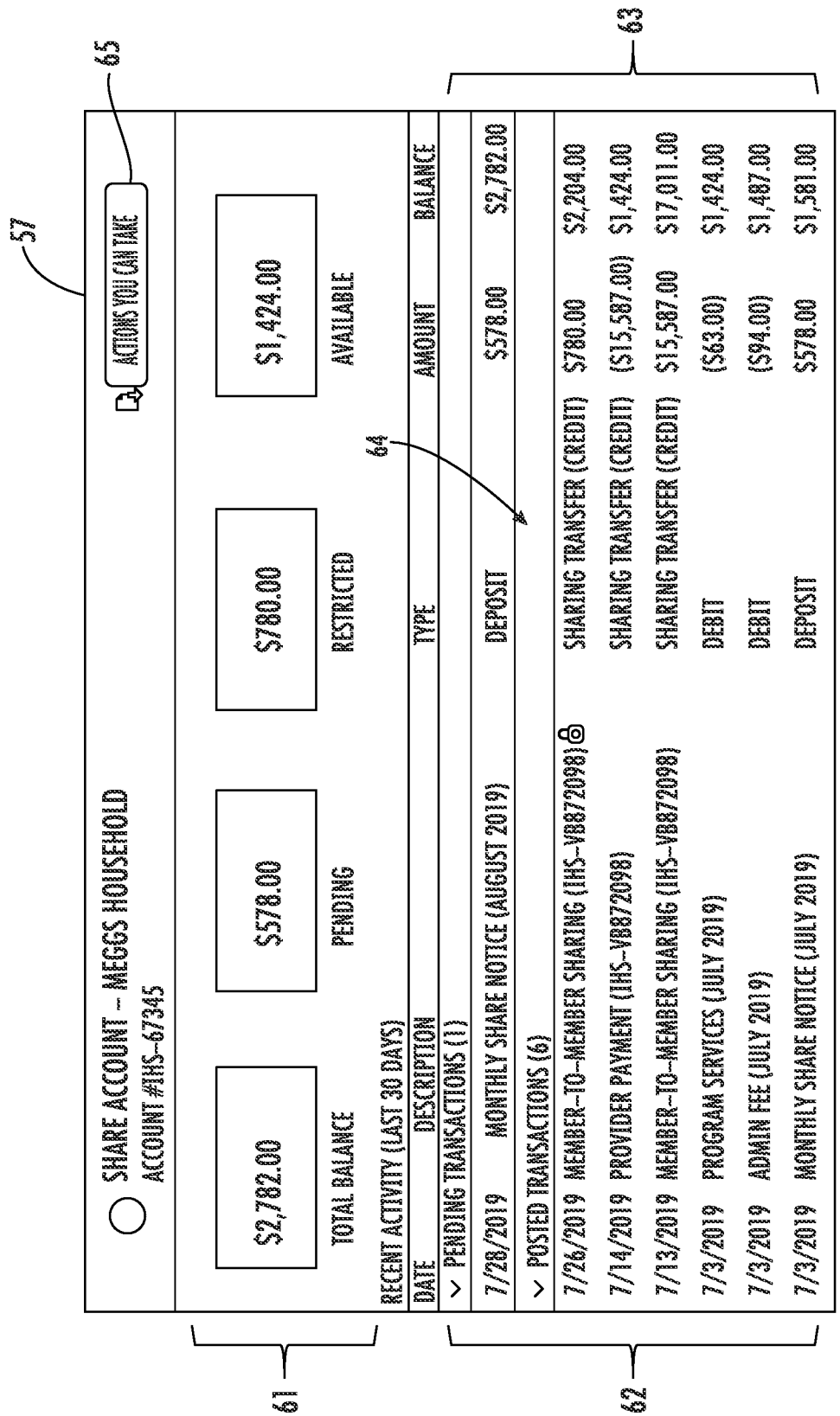
FIG. 6 is a display view of a Graphical User Interface (GUI) generated by the computing device of FIG. 3 for a bill owner in accordance with an example embodiment.

The links enable the sharing network to create and provide members 36 with a unique view into the P2P sharing process that transacts through their share accounts 33. The view of a member share account from the perspective of a bill owner is provided in the GUI 57, which is shown in further detail in FIG. 6. Like any financial account, a summary view of the account balance is provided in section 61. The total balance is broken down into three parts, namely (1) pending balance represents funds that have not settled, (2) restricted balance represents funds tied to one or more virtual bill accounts, and (3) available balance represents settled funds that may be allocated by the sharing network for member sharing or withdrawn by the member. Transactions related to the member share account are detailed by transaction type and description in section 62, and the transaction amounts and running balance is detailed as well in section 63. The member share account also provides the member 36 with access to initiate certain account activities, here via a pull-down menu 65.

In the case of the bill owner, transactions 64 are displayed as a credit because they represent funds shared by the contributors to pay a medical bill of the bill owner's household. The $780.00 sharing transfer transaction 64 represents shared funds collected in virtual bill account #IHS-VB872098 for a household member of the network member (Anthony Meggs). However, all sharing transactions related to virtual bill account #IHS-VB872098 have NOT been completed as indicated by the "padlock" icon, thus making the $780.00 restricted funds, which cannot be accessed by the network member or transferred to the bill service provider. This feature of virtual bill accounts 46 helps provide greater transparency and engagement in the P2P sharing process, which is the ability to display the "aggregated sum" of sharing transactions as a single sharing transfer credit in the member share account of the bill owner when the receipts span many contributors over a period of time.

Another feature that helps improve transparency and engagement is the ability to easily view the many transactions and contributors behind the single sharing transfer credit transaction 64 in the member share account of the bill owner. As illustrated in FIG. 7, virtual bill accounts 46 enable sharing networks to deploy member share accounts that allow members to access P2P sharing details at the touch of a button. In the illustrated example, the $780.00 sharing credit is hyperlinked to a detailed pop-out GUI 60 view of the virtual bill account #IHS-VB872098. The detailed view provides the bill owner with an awareness as to who is contributing and sharing in the medical bills of the member's household. Moreover, in some configurations a social view may be provided (not shown) in which images of contributors are provided, along with information about them (location, etc.) and the ability to chat or send messages between them to engage in social interactions and communications that drive greater engagement and a social transparency into the P2P sharing process.

Figure 9:
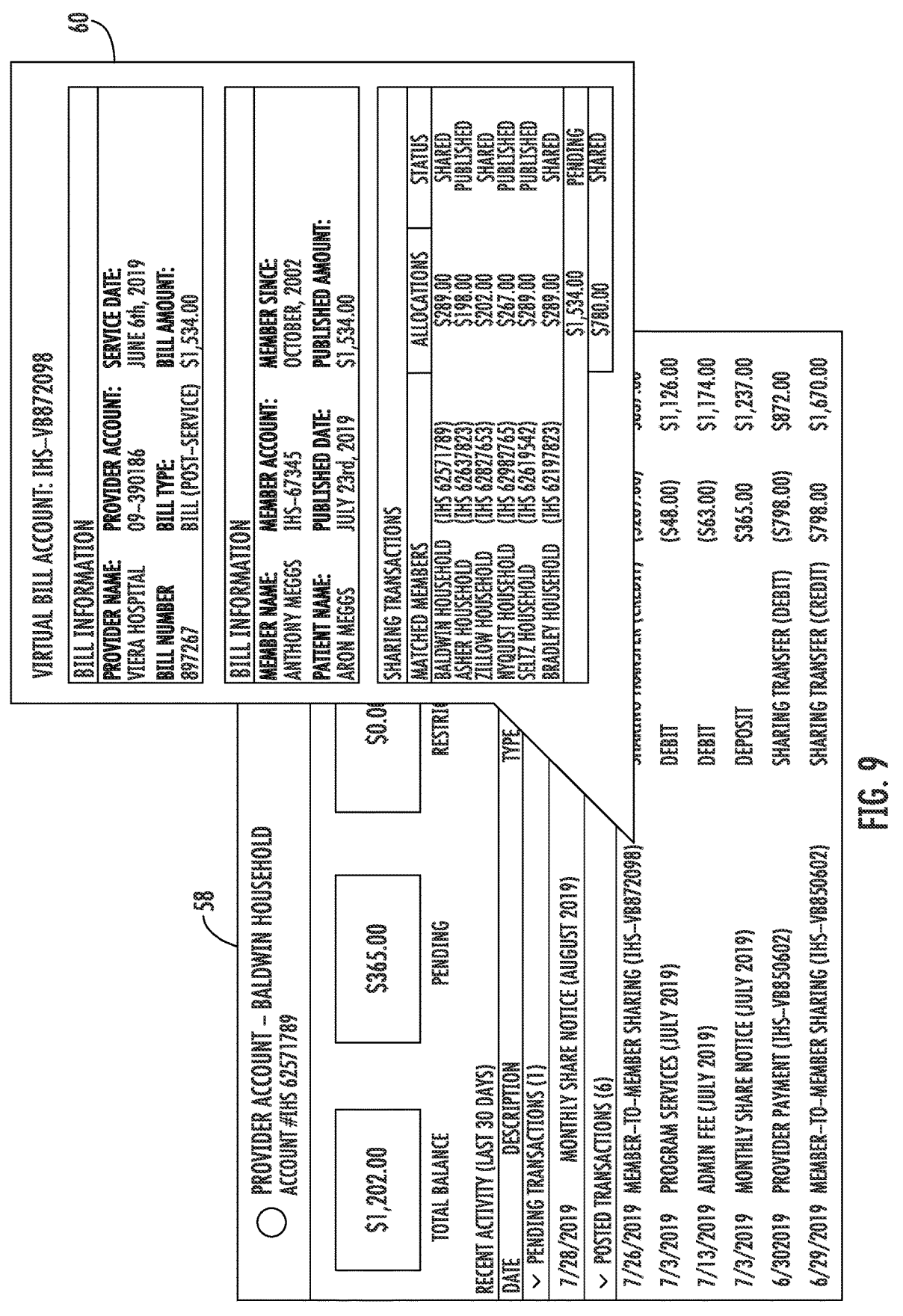

Still another feature that helps promote greater engagement and transparency is that the bill contributors benefit from the same enabling account linking capabilities associated with virtual bill accounts 46. In the case of healthcare sharing, members 36 are both bill owners and bill contributors, often at the same time. So, as illustrated in FIG. 8, member share accounts will also display sharing transactions, from a bill contributor point of view, as a single transaction. However, the transaction is registered as a debit, and that debit represents the actual allocated amount that the VSE module 37 has transferred from the bill contributor's share account 33 and settled in the virtual bill account 46. In the illustrated example, the $289.00 sharing transfer debit transaction 71 is the allocated amount that the Baldwin household has contributed to the Meggs household and settled in virtual bill account #IHS-VB872098. Just as a bill owner transaction, the bill contributor transaction is hyperlinked to the virtual bill account 46 so that the GUI 60 will be displayed as a pop-out window (FIG. 9) for easy access to the detailed sharing transactions of the member medical bill 38 (or pre-service request 41). Thus, network members 36 are given visibility into the members 36 that their contribution has helped, as well all other contributors to the member bill 38.

Lastly, the bill linking feature of virtual bill accounts enables Healthcare sharing networks to engage the medical provider into the sharing process that gives them access and transparency that they desire. Networks that invite Providers to open accounts on their VSE Platform, or join a payor service that integrates the VSEs of multiple sharing networks, will equip providers with a unique view into the P2P sharing process. Provider accounts, as illustrated in FIG. 15, can provide medical providers with a summary view into all their patient bills being processed by sharing networks (FIG. 15, Section 15.1). total bills represents the value of all "bill in publishing", plus all "shared and available bills". Bills in Publishing represents the total published amount of patient bills that are not yet fully shared. "Shared and available" represents patient bills that have been fully shared, but not yet withdrawn by the provider. A detailed transactional list of all patient bills is provided (FIG. 15, Section 15.2), as well as their published amounts and a running account balance (FIG. 15, Section 15.3). The provider account also provides access to initiate withdrawal of funds (payments) for patient bills that have been fully shared (FIG. 15, Section 15.5). Like member share accounts, the transactional list of patient bills provides a hyper-link to the detailed virtual bill account associated with each patient bill. Also, like the member share accounts, the detailed view of the virtual bill account provides the medical provider a view of all the bill contributors who shared in the payment of the patient's bills. This level of transparency engages medical providers into the sharing process and builds their confidence in healthcare sharing as a credible payment option.

Virtual bill accounts 46 also help enhance the security and protection of the P2P sharing process. In the case of healthcare sharing, networks members are happy to participate in a sharing process that is easy to manage, saves them money and is credible. In addition to the cost savings, another valued benefit cited by members 36 is the social satisfaction in knowing that their money is going directly to another member and not to the profits of an insurance company. The use of virtual bill accounts insures members 36 that their funds are going directly for the payment of another's member bill. As previously noted, though funds contributed to a member medical bill 38 are displayed in the share account of the bill owner as a sharing credit transaction 64, those funds are actually held in a separate virtual bill account 46 for the purpose of sharing and paying the bill owner's household bill. In fact, even though funds have been contributed to the bill owner for the payment of a bill, access to the funds have been restricted as noted in the restricted balance (FIG. 10, Section 10.1) and indicated by the "padlock" icon appended to the sharing credit transaction 64. Thus, network members 36 have confidence in knowing that "shared funds" are NOT available to the bill owner for withdrawal. Network members are assured that the dollars they share for another member's medical bill 38 (or pre-service request 41) is certain to go to the medical provider as payment.

Likewise, in the provider account 44 displayed in the GUI 59 (FIG. 10), payment for patient bills 38 that have been published for sharing appear as a restricted credit amount. Published bills that have not yet been fully shared are placed in a "pending" status in the provider account 44 and are restricted as noted by the "padlock" icon. Also, like the bill owner view, the provider account 44 has not actually been credited the bill amount as this point. In reality, any settled contributions still reside in the virtual bill account. However, the account linking feature of virtual bill accounts 46 enables sharing networks to display published bills 38 (or pre-service requests 41) as a pending payment in the provider account. This gives the provider, as well as the contributors, a sense of confidence and security that a patient's bill 38 has been received and published for sharing, and that any contributed amounts are being collected in a virtual bill account 46 that has been created and linked to the provider for the purpose of paying the provider the published amount.

Furthermore, the security and protections provided by the VSE module 37 and the virtual bill accounts 46 accommodate the fact that sometimes the sharing network pre-pays or escrows funds for expensive procedures before services can be rendered (i.e., for pre-service escrow requests 41). In this case, sharing networks can allocate, publish and share the pre-service bill or quote 41 and hold collected funds in the virtual bill account 46 that was created for the procedure. By linking the virtual bill account 46 to the provider account 44, the pre-service bill 41 is seen as a "pending" credit transaction that is restricted. Thus, the provider has a sense of security that the bill has been funded and the network members are secure knowing that the dollars are not released from the virtual bill account 46 until the service has been rendered.

The VSE platform 31 may be implemented using one or more computing devices such as servers, network interface devices, client devices, etc., including the appropriate hardware (e.g., processor, memory, etc.) and software having non-transitory computer-readable instructions for performing the operations discussed herein. Moreover, in some embodiments the VSE platform 31 may be implemented within a cloud computing network, as discussed above. Moreover, it will be appreciated that the systems and methods set forth herein may also be used with other types of cost or expense sharing platforms besides healthcare sharing networks, such as automotive repair bills, home appliance repair bills, veterinary bill sharing, etc. That is, the VSE platform 31 may also support other share networks beyond just health care sharing.

Many modifications and other embodiments will come to the mind of one skilled in the art having the benefit of the teachings presented in the foregoing descriptions and the associated drawings. Therefore, it is understood that the foregoing is not to be limited to the example embodiments, and that modifications and other embodiments are intended to be included within the scope of the appended claims.

That which is claimed is:

1. A computing device comprising:
a memory and a processor configured to cooperate with the memory to operate a virtual share exchange (VSE) platform by
establishing member sharing accounts on the VSE platform for respective members of the VSE platform for receiving electronic deposits from the respective members from external payment sources to be used for sharing payment of member healthcare bills across a plurality of the member sharing accounts, the member sharing accounts having unique identifiers (IDs),
establishing healthcare provider accounts on the VSE platform for healthcare providers issuing member healthcare bills,
receiving a given member healthcare bill issued by a given healthcare provider,
matching and allocating payment amounts of the given member healthcare bill to member sharing accounts on a member-to-member basis based upon member agreement to share in payment of the given member healthcare bill,
dynamically generating in real time a single purpose table in a database on the VSE platform responsive to receiving the given member healthcare bill submitted for payment sharing corresponding to the given healthcare provider, the single purpose table defining a temporary virtual bill account solely for reconciliation of the respective member healthcare bill, the temporary virtual bill account being externally addressable through a routing number and a unique account number,
the single purpose table linking the given member healthcare bill to the unique IDs of the member sharing accounts of members sharing in the given member healthcare bill so that transactions in the temporary virtual bill account are viewable to members sharing in the given member healthcare bill,
electronically transferring funds from the member sharing accounts to the healthcare provider account for the given healthcare provider that issued the given member healthcare bill using the externally addressable routing number and unique account number of the temporary virtual bill account based upon the single purpose table and without transferring the funds between the member sharing accounts, and
closing and archiving the virtual bill account upon electronically transferring the funds to the healthcare provider account for the given healthcare provider that issued the member healthcare bill, the archived virtual bill account providing an auditable ledger for the transactions in the temporary virtual bill account.

2. The computing device of claim 1 wherein the processor is further configured to generate graphical user interfaces (GUIs) for viewing the transactions in the temporary virtual bill account.

3. The computing device of claim 2 wherein the GUIs display an aggregated sum of the transactions as a single sharing transfer credit to be transferred to the healthcare provider account of the given healthcare provider that issued the given member healthcare bill.

4. The computing device of claim 3 wherein the GUIs further display all of the transactions that contribute to the aggregated sum of the transactions.

5. The computing device of claim 1 wherein the processor is further configured to publish the allocated payment amounts to each of the member sharing accounts of members sharing in the payment of the member healthcare bill during a publishing period, and wherein the electronically transferring of funds comprises electronically transferring after the publishing period has expired.

6. The computing device of claim 1 wherein the processor is further configured to receive pre-payment requests issued by the healthcare providers for funding prior to performing healthcare services, and configured to dynamically generate in real time single purpose tables defining temporary virtual bill accounts for payment sharing for the pre-payment requests.

7. A method comprising:
   establishing member sharing accounts at a server defining a virtual share exchange (VSE) platform for respective members of the VSE platform for receiving electronic deposits from the respective members from external payment sources to be used for sharing payment of member healthcare bills across a plurality of the member sharing accounts, the member sharing accounts having unique identifiers (IDs);
   establishing, at the server, healthcare provider accounts on the VSE platform for healthcare providers issuing the member healthcare bills;
   receiving, at the server, a given member healthcare bill issued by a given healthcare providers;
   matching and allocating, at the server, payment amounts of the given member healthcare bill to member sharing accounts on a member-to-member basis based upon member agreement to share in payment of the given member healthcare bill;
   dynamically generating in real time a single purpose table in a database on the VSE platform responsive to receiving the given member healthcare bill submitted for payment sharing at the server corresponding to the given healthcare provider, the single purpose table defining a temporary virtual bill account solely for reconciliation of the respective member healthcare bill, the temporary virtual bill account being externally addressable through a routing number and a unique account number;
   the single purpose table linking the given member healthcare bill to the unique IDs of the member sharing accounts of members sharing in the given member healthcare bill so that transactions in the temporary virtual bill account are viewable to members sharing in the given member healthcare bill;
   at the server, electronically transferring funds from the member sharing accounts to the healthcare provider account for the given healthcare provider that issued the given member healthcare bill using the externally addressable routing number and unique account number of the temporary virtual bill account at the server based upon the single purpose table and without transferring the funds between the member sharing accounts; and
   closing and archiving the virtual bill account, at the server, upon electronically transferring the funds to the healthcare provider account for the given healthcare provider that issued the member healthcare bill, the archived virtual bill account providing an auditable ledger for the transactions in the temporary virtual bill account.

8. The method of claim 7 further comprising, at the server, generating graphical user interfaces (GUIs) for viewing the transactions in the temporary virtual bill account.

9. A non-transitory computer-readable medium for a server having a processor and having computer-executable instructions for causing the processor to perform steps comprising:
   establishing member sharing accounts defining a virtual share exchange (VSE) platform for respective members of the VSE platform for receiving electronic deposits from the respective members from external payment sources to be used for sharing payment of member healthcare bills across a plurality of the member sharing accounts, the member sharing accounts having unique identifiers (IDs);
   establishing healthcare provider accounts on the VSE platform for healthcare providers issuing the member healthcare bills;
   receiving a given member healthcare bill issued by a given healthcare provider, and
   matching and allocating payment amounts of the given member healthcare bill to member sharing accounts on a member-to-member basis based upon member agreement to share in payment of the given member healthcare bill;
   dynamically generating in real time a single purpose table in a database on the VSE platform dynamically generating in real time a single purpose table in a database on the VSE platform responsive to receiving the given member healthcare bill submitted for payment sharing corresponding to the given healthcare provider, the single purpose table defining a temporary virtual bill account solely for reconciliation of the respective member healthcare bill, the temporary virtual bill account being externally addressable through a routing number and a unique account number;
   the single purpose table linking the given member healthcare bill to the unique IDs of the member sharing accounts of members sharing in the given member healthcare bill so that transactions in the temporary virtual bill account are viewable to members sharing in the given member healthcare bill;
   electronically transferring funds from the member sharing accounts to the healthcare provider account for the given healthcare provider that issued the given member healthcare bill using the externally addressable routing number and unique account number of the temporary virtual bill account based upon the single purpose table and without transferring the funds between the member sharing accounts; and
   closing and archiving the virtual bill account upon electronically transferring the funds to the healthcare provider account for the given healthcare provider that issued the member healthcare bill, the archived virtual bill account providing an auditable ledger for the transactions in the temporary virtual bill account.

10. The non-transitory computer-readable medium of claim 9 further having computer executable instructions for causing the server to perform a step comprising generating graphical user interfaces (GUIs) for viewing the transactions in the temporary virtual bill account.

* * * * *